(12) United States Patent
Philippe et al.

(10) Patent No.: US 6,258,977 B1
(45) Date of Patent: Jul. 10, 2001

(54) ALKYL3-OXOALKANOATES

(75) Inventors: Michel Philippe, Wissous; Bernadette Luppi, Sevran; Didier Semeria, Courtry; Claude Mahieu, Paris, all of (FR)

(73) Assignee: L'Oreal (FR)

( * ) Notice: Subject to any disclaimer, the term of this patent is extended or adjusted under 35 U.S.C. 154(b) by 0 days.

(21) Appl. No.: 09/348,677

(22) Filed: Jul. 6, 1999

Related U.S. Application Data

(63) Continuation of application No. 08/731,309, filed on Oct. 15, 1996, now Pat. No. 6,090,974.

(30) Foreign Application Priority Data

Oct. 13, 1995 (FR) .................................................. 95 12041

(51) Int. Cl.[7] .................................................. C07C 69/66
(52) U.S. Cl. ............................ 560/174; 560/51; 560/53; 560/54; 560/176; 560/178; 560/9; 560/10; 560/15; 560/147
(58) Field of Search ................................ 560/51, 53, 54, 560/174, 176, 178, 9, 10, 15, 147

(56) References Cited

U.S. PATENT DOCUMENTS 4,206,120   6/1980   Hunt .................................. 260/245.3

FOREIGN PATENT DOCUMENTS

| 887652 | 7/1953 | (DE) . |
| 500437 | 8/1992 | (EP) . |
| 646 572 | 4/1995 | (EP) . |

OTHER PUBLICATIONS

G. Gregory et al., "Synthesis of Racemic 2–Amino–octadecane–I : 3–diols," Journal of the Chemical Society, Part III., pp. 2453–2456 (1951).

Zav'ualov et al., "Reactions. . . sodium thioacetate", Izv. Akad. Nauk SSSR, Ser. Khim., (8), p. 1920 (1982).

M. Viscontini, "Reduction des substances, Beta–amino–alpha, gamma–dicarbonylees; une nouvelle synthese de l'allo–DL–phenyl–3–amino–2–propane–diol–1,3 (DL–erythro–phenylserinol)," *Helvetica Chimica Acta*, vol. XXXV, Oct. 1952, pp. 1803–1805.

March, "Reduction of Nitroso Compounds and Hydroxylamines to Amines," *Advanced Organic Chemistry*, 1985, John Wiley & Sons, 3d Ed., p. 1105.

Houben–Weyl, Reduktion von Oximen (Isonitros overbindungen) und Hydroxylaminen, *Methoden der Organischen Chemie*, vol. XI/1, 1957, pp. 495–506.

Sisido et al., "Synthesis of Racemic Phytophingosine and the lyxo Isomer," *Journal of Organic Chemistry*, vol. 34, No. 11, Nov. 1969, pp. 3539–3544.

*Chemical Abstracts*, vol. 98, No. 1, Jan. 3, 1983, "Reactions of Esters of Alpha–(Bromoacyl)Acetic Acid with Sodium Thioacetate," p. 4452, Column R, Abstract No. 4451u.

*Journal of the Chemical Society*, Perking Transactions 1, No. 2, Feb. 1987, pp. 333–343, Leslie Crombie et al., "Synthesis of the Mammea Coumarins, Part 2, Experiments in the Mammea E Series and synthesis of Mammea E/AC".

*Journal of Organic Chemistry*, vol. 43, No. 10, May 12, 1978, pp. 2087–2088, Yuji Oikawa et al., "Meldrum's Acid in Oganic Chemistry 2: A General and Versatile Synthesis of Beta–Keto Esters".

Anisari et al., "Peracid oxidation . . . fatty acids" Chem. Phys. Lipids, 29(1), pp. 45–53 (1981).

Ansari et al., Peracid oxidation of . . . fatty acids, Chem. Phys. Lipids, 29(1), pp. 45–53, 1981. No month provided.*

Zav'yalov et al., Reactions . . . sodium thioacetate, Izv. Akad. Nauk SSSR, Ser. Khim., (8), p. 1920, 1982. No month provided.*

* cited by examiner

Primary Examiner—Rosalynd Keys
(74) Attorney, Agent, or Firm—Finnegan Henderson Farabow, Garrett & Dunner

(57) ABSTRACT

An alkyl 3-oxoalkanoate, a process for preparation and use for the synthesis of fatty hydroxylated amino acids, fatty amino alcohols and ceramides.

7 Claims, No Drawings

ALKYL 3-OXOALKANOATES

This is a continuation of application Ser. No. 08/731.309 filed Oct. 15, 1996 now U.S. Pat. No. 6,090,974 which is incorporated herein by reference.

The invention relates to an alkyl 3-oxoalkanoate, to a process for the preparation thereof and to the use thereof for the synthesis of amino acids, amino alcohols and ceramides. Applicants specifically incorporate by reference copending application Ser. No. 08/732,573, PROCESS FOR THE PREPARATION OF 2-AMINOALKANE-1,3,4-TRIOLS of Didier Semeria, Bernadette Luppi, and Michel Philippe, filed on Oct. 15, 1996. A copy of this incorporated-by-reference-application is attached as Appendix A.

In the natural state, ceramides are the main components of the lipid layers of the epidermis. They are used in cosmetics, in natural or synthetic form, in compositions intended, inter alia, to reduce skin dryness or to impart better elasticity to the skin, or alternatively compositions intended for treating the hair.

Natural ceramides are generally obtained by extraction from pig skin, cow brain, eggs, blood cells and plants (JP 86/260008 or JP 87/120308).

The many drawbacks associated with this type of supply (fragility, contamination, storage, cost, etc.) are such that the chemical synthesis route was very soon explored.

However, synthetic routes which allow industrial development within acceptable cost limits are rare.

The industrial-scale preparation of fatty hydroxylated amino acids and of fatty amino alcohols exhibits the same difficulties.

Thus, it is with surprise that the inventors discovered novel compounds, which are easy to synthesize and which can readily be used for the preparation of ceramides, fatty hydroxylated amino acids, 2-amino-3,4-diol alkanoic acids, fatty amino alcohols and 2-aminoalkane-1,3,4-triols.

The subject of the present invention is an alkyl 3-oxoalkanoate corresponding to formula (I):

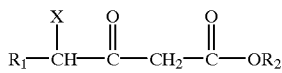
(I)

wherein: $R_1$ is selected from linear and branched alkyl radicals containing from 6 to 28 carbon atoms, linear and branched alkenyl radicals containing from 6 to 28 carbon atoms, and linear and branched aralkyl radicals containing from 4 to 28 carbon atoms, wherein $R_1$ may be interrupted by at least one ether bridge, and further wherein $R_1$ optionally bears at least one function selected from hydroxyl functions and $C_1$ to $C_8$ acyloxy functions;

$R_2$ is selected from linear and branched alkyl radicals containing from 1 to 5 carbon atoms and linear and branched alkenyl radicals containing from 2 to 5 carbon atoms; and X represents a leaving group.

The term "leaving group" denotes a group such as those mentioned by Jerry March in "Advanced Organic Chemistry", Wiley Interscience, 3rd edition, p.315, Table 10, the disclosure of which is specifically incorporated by reference herein.

Products of formula (I) preferably satisfy at least one of the following conditions:

$R_1$ represents an alkyl radical or an alkenyl radical, which is linear or branched, comprising from 10 to 18 carbon atoms, optionally bearing at least one hydroxyl function, $R_2$ represents an easily hydrolysable alkyl radical such as, for example, a methyl or ethyl radical, X denotes a chlorine or bromine or iodine atom, or a sulphonate group.

Even more preferably, X denotes a bromine atom.

When $R_1$ is selected from linear and branched aralkyl radicals, said radicals preferably contain 5 to 28 carbon atoms and more preferably contain 6 to 28 carbon atoms.

When $R_1$ represents aralkyl radicals, said radicals are preferably carbocyclic aralkyl radicals.

The subject of the invention is also a process for the preparation of a alkyl 3-oxoalkanoate derivative of formula (I), characterized in that a malonic derivative is reacted with an acylating agent.

The term "malonic derivative" preferably denotes a monoester or a diester of malonic acid such as, for example, the diisopropylidene ester of malonic acid, also referred to as Meldrum's acid, or the potassium salt of ethyl malonate. Meldrum's acid will preferably be used.

The term "acylating agent" preferably denotes compounds corresponding to formula (II):

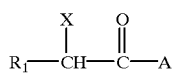
(II)

wherein:

$R_1$ is selected from linear and branched alkyl radicals containing from 6 to 28 carbon atoms, linear and branched alkenyl radicals containing from 6 to 28 carbon atoms, and linear and branched aralkyl radicals containing from 4 to 28 carbon atoms, wherein $R_1$ may be interrupted by at least one ether bridge, and further wherein $R_1$ optionally bears at least one function selected from hydroxyl functions and $C_1$ to $C_8$ acyloxy functions; X represents a leaving group; and A is selected from

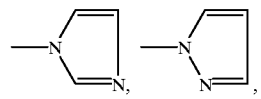

halogens; groups

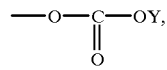

wherein Y is a $C_2$ to $C_8$ alkyl radical; alkoxy groups —OZ, wherein Z denotes $C_1$–$C_8$ alkyl radicals;

para-nitrophenyl radicals;

succinimidyl radicals; and dicyclo-hexylcarbodiimidyl radicals.

Preferably, X represents a bromine atom and A is a chlorine atom.

The products corresponding to formula (II) described above are prepared by activation of the corresponding acid, i.e. from a product of formula (II) with A=OH, by acid-activation means which are well known to those skilled in the art. The products corresponding to formula (II) with A=OH are commercially available products.

The reaction of the process for the preparation of the products of formula (I) is preferably carried out in anhydrous medium.

It is preferably performed in a suitable solvent such as, for example, tetrahydrofuran, dichloromethane, pyridine or tert-butyl methyl ether.

The subject of the invention is also the use of an alkyl 3-oxoalkanoate derivative of formula (I) for the preparation of ceramides, fatty hydroxylated amino acids and fatty amino alcohols.

For example, X may be substituted by a group

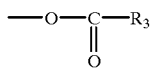

wherein $R_3$ is selected from linear and branched alkyl radicals containing from 1 to 6 carbon atoms, linear and branched alkenyl radicals containing from 2 to 6 carbon atoms, and aryl radicals containing 6 carbon atoms, which will then be followed by an oximation of the methylene group to obtain a compound of formula (III):

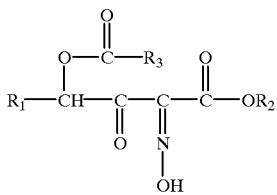

(III)

wherein
$R_1$, $R_2$ and $R_3$ are the same as defined above.

Starting with the compounds of formula (III) and by successive methods of reduction which are well known to those skilled in the art, a 2-amino-1,3,4-triol, or one of its amine salts, may be obtained, corresponding to formula (IV).

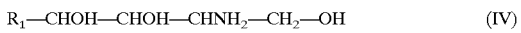

(IV)

Thus, it will be possible, for example, to use the reduction methods employed by Posternik (Chem. Phys. Lipids 1971, 7, 135–143), Isida (J. Org. Chem. 1969, 34, 3539–3544) and Jager (Agnew. Chem. Int. Ed. Engl. 1981, 20, 601–605), the disclosures of which are specifically incorporated by reference herein, for the synthesis of amino- alkane triols.

For example, a compound of formula (III) may be treated with hydrogen under pressure in the presence of a catalyst or with nascent hydrogen generated by zinc in the presence of an acid such as, for example, acetic acid.

In a similar manner, hydroxylated fatty amino acids may be prepared by treating the compounds of formula (III) with reducing agents chosen from: hydrogen under pressure in the presence of a catalyst; and nascent hydrogen generated by zinc in the presence of an acid such as, for example, acetic acid.

Starting with the compounds of formula (III), ceramides may also be synthesized directly by a two-step process which comprises converting an alkyl 2-hydroxyimino-3-oxo-4-alkanoyloxyalkanoate into alkyl 2-alkanoylamido-3-oxo4-alkanoyloxyalkanoate by reduction and acylation of the oxime, and then in reducing the ester and ketone functions to alcohol, for example by treatment with sodium borohydride.

Reference may be made, for example, to document EP-A-646,572 which gives examples of such syntheses. This disclosure is specifically incorporated by reference herein. Reference may also be made to Soukup (Helv. Chim. Acta, 70, 232–236, 1987) for the reactions of oximation, reduction of the oxime and acylation of the amine which make it possible to prepare an alkyl 2-alkanoylamido-3-oxo4-alkanoyloxyalkanoate from the products according to the invention. This disclosure is specifically incorporated by reference herein.

The compound of formula (IV) obtained according to the invention may be used in-synthetic processes which can lead to ceramides such as those described by Shapiro, D. (Chemistry of sphingolipids, Hermann, Paris, 1969, p 26–34). This disclosure is specifically incorporated by reference herein.

The example which follows illustrate the present invention without, however, limiting the scope thereof.

EXAMPLE 1

Synthesis of methyl 4-bromo-3-oxooctadecanoate 1.8 mol of Meldrum's acid were mixed with 3.96 mol of pyridine in a round-bottomed flask containing 1,2-dichloroethane, placed at 0° C. under argon and with stirring. 1.98 mol of 2-bromohexadecanoyl chloride were then introduced slowly and the mixture was left stirring for 2 hours at 0° C.

The solution was then washed three times with water and dried, the solvent was evaporated off and the residue was taken up in methanol. The solution in methanol was maintained at reflux for two hours and the solvent was then evaporated off under vacuum.

The methyl 4-bromo-3-oxooctadecanoate was then purified on a column of silica. 494 g of methyl 4-bromo-3-oxooctadecanoate were thus recovered in the form of a mixture of the keto (k) 40% and enol (e) 60% forms. NMR spectra:

$^1$H spectrum (CDCl$_3$):

d=0.87, t, CH3 (k+e); d=1.25–1.6, m, —(CH2)$_{12}$-(k+e); d=1.8–2.12, m, (C13 H27)—CH2—CHBr (k+e); d=3.63–3.83, ab, —CH2—CO$_2$CH3 (k); d=3.74–3.76, 2s, OCH3 (k+e); d=4.21, m, CHBr (e); d=4.43, dd, CHBr (k); d=5.23–5.29, 2s, =CH—CO2CH3 (e); d=11.96–11.97, broad s, OH (e).

$^{13}$C spectrum (CDCl$_3$);

d=14.06, CH3; d=22.66, CH3—CH2; d=27.14, C12H25—CH2-(k); d 27.53, C12H24—CH2 (e); d=28.8–29.66, —(CH2)$_9$—; d=31.9, C2H5—CH2—; d=32.97, —CH2—CHBr (k); d=35.5, —CH2—CHBr (e); d=45.19, —CH2CO2CH3 (k); d=49.91, —CHBr (e); d=51.53, OCH3 (e); d=52.43, OCH3 (k); d=53.3, —CHBr (k); d=89.83, OCH3 (e); d=167.34, —CO2CH3 (k); d=172.65–173.69, =COH and —CO2CH3 (e); d=196.01, —CO— (k).

We claim:

1. An alkyl 3-oxoalkanoate corresponding to formula (I):

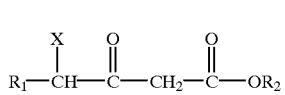

(I)

wherein:

$R_1$ is chosen from linear and branched alkyl radicals containing from 6 to 28 carbon atoms, linear and branched alkenyl radicals containing from 6 to 28 carbon atoms, and linear and branched aralkyl radicals containing from 4 to 28 carbon atoms, wherein $R_1$ may or may not be interrupted by at least one ether bridge, and further wherein $R_1$ may or may not contain at least one function chosen from hydroxyl functions and $C_1$ to $C_8$ acyloxy functions;

$R_2$ is chosen from linear and branched alkyl radicals containing from 1 to 5 carbon atoms and linear and branched alkenyl radicals containing from 2 to 5 carbon atoms; and X is a leaving group chosen from chlorine, bromine, iodine, and a sulphonate group.

2. An alkyl 3-oxoalkanoate according to claim 1, wherein $R_1$ is chosen from linear and branched alkyl radicals containing from 10 to 18 carbon atoms and linear and branched alkenyl radicals containing from 10 to 18 carbon atoms.

3. An alkyl 3-oxoalkanoate according to claim 1, wherein $R_1$ bears at least one hydroxyl function.

4. An alkyl 3-oxoalkanoate according to claim 1, wherein said aralkyl radicals are carbocyclic aralkyl radicals.

5. An alkyl 3-oxoalkanoate according to claim 1, wherein $R_2$ is chosen from a methyl radical and an ethyl radical.

6. An alkyl 3-oxoalkanoate according to claim 1, wherein X is a leaving group chosen from bromine, iodine, and a sulphonate group.

7. An alkyl 3-oxoalkanoate according to claim 6, wherein X is a bromine atom.

* * * * *